(12) United States Patent
Li

(10) Patent No.: US 11,148,960 B2
(45) Date of Patent: Oct. 19, 2021

(54) UV STERILIZATION CUP

(71) Applicant: Xiaohul Li, Shenzhen (CN)

(72) Inventor: Xiaohul Li, Shenzhen (CN)

( * ) Notice: Subject to any disclaimer, the term of this patent is extended or adjusted under 35 U.S.C. 154(b) by 171 days.

(21) Appl. No.: 16/538,807

(22) Filed: Aug. 12, 2019

(65) Prior Publication Data

US 2020/0216332 A1   Jul. 9, 2020

(30) Foreign Application Priority Data

Jan. 7, 2019   (CN) .......................... 201910010430.4

(51) Int. Cl.
| | |
|---|---|
| *C02F 1/32* | (2006.01) |
| *A61L 2/10* | (2006.01) |
| *A61L 2/26* | (2006.01) |
| *C02F 1/00* | (2006.01) |
| *C02F 1/28* | (2006.01) |

(52) U.S. Cl.
CPC ................ *C02F 1/325* (2013.01); *A61L 2/10* (2013.01); *A61L 2/26* (2013.01); *C02F 1/001* (2013.01); *C02F 1/283* (2013.01); *A61L 2202/11* (2013.01); *A61L 2202/122* (2013.01); *C02F 2201/326* (2013.01); *C02F 2201/3222* (2013.01); *C02F 2303/04* (2013.01)

(58) Field of Classification Search
CPC ...... C02F 1/72; C02F 1/78; C02F 1/48; C02F 1/46; A61L 2/10; B01D 32/34; B01D 61/10; B01D 61/08
See application file for complete search history.

(56) References Cited

U.S. PATENT DOCUMENTS

2015/0307368 A1* 10/2015 Yanke ..................... C02F 1/325
                                                              210/660

FOREIGN PATENT DOCUMENTS

WO    WO-2014187524 A1 * 11/2014   .............. C02F 1/325

* cited by examiner

*Primary Examiner* — Walter D. Griffin
*Assistant Examiner* — Cameron J Allen

(57) ABSTRACT

A UV sterilization cup includes a cup body with a first opening thereof, a cup shielding covered on the first opening, a filter matched with the first opening, a UV sterilization member received in the cup shielding for sterilizing water and a waterproof transparent member received in the cup shielding for sealing the UV sterilization member. The UV sterilization member includes a UV PCB and a UV light source connected to the UV PCB. The UV PCB includes a UV generating circuit formed thereon to drive the UV light source to emit ultraviolet ray so as to sterilize water received in the cup body. The compact structure can achieve a reliable sterilization effect with 99.9% by setting the UV light source, and water fetched in outdoors can reach the standard of healthy drinking water that it is first filtered by the filter and then sterilized by the UV light source.

17 Claims, 13 Drawing Sheets

UV STERILIZATION CUP

BACKGROUND

1. Technical Field

The present disclosure generally relates to cups field, and especially relates to a UV sterilization cup.

2. Description of Related Art

On the earth, all kinds of microbe are affecting our life all the time, and a large proportion of them can pose a major threat to our health, thereby a plurality of sterilization means and methods is appeared in order to protect our health. However, such sterilization means and methods used at present all have problems such as large area of equipments, unsatisfactory sterilization efficiency, long time, high cost and secondary pollution of environment. Drinking water is generally boiled to kill bacteria. However, such method can't effectively kill some tough bacteria with strong vitality, and the boiled water may be inevitably contaminated by secondary pollution during its cooling process.

A conventional sterilization method of drinking water is first filtered and then heated to achieve boiling water, finally it can only be drank after cooling it. But, according to long-term researches, the water fetched in outdoors after it is filtered and heated can still contain a lot of bacteria, which is not effective in killing bacteria.

SUMMARY

The technical problems to be solved: in view of the shortcomings of the related art, the present disclosure relates to a UV sterilization cup which can achieve a good sterilization effect with 99.9% by a compact structure, at the same time, water fetched in outdoors can reach the standard of healthy drinking water that it is first filtered by the filter and then sterilized by the UV light source.

The technical solution adopted for solving technical problems of the present disclosure is:

a UV sterilization cup includes a cup body and a cup shielding covered on the cup body. The cup body includes a first receiving room with a first opening being formed on its portion adjacent to the cup shielding. The cup shielding includes a second receiving room with a second opening being formed on its end adjacent to the cup body and connected to the first opening. The UV sterilization cup further includes a UV sterilization member received in the second receiving room to emit ultraviolet ray for sterilizing water received in the cup body, and a waterproof transparent member received in the cup shielding and adjacent to the first receiving room for sealing the UV sterilization member. The UV sterilization member includes a UV PCB installed in one end of the second receiving room away from the second opening, and a UV light source electrically connected to a UV generating circuit of the UV PCB and installed in the other end of the second receiving room adjacent to the second opening. The waterproof transparent member is provided to block connection between the first receiving room and the second receiving room. The waterproof transparent member is also mounted on a bottom end of the UV light source to abut against the bottom end of the UV light source and configured to transmit the ultraviolet ray emitted from the UV sterilization member into the first receiving room.

Wherein a wall of the cup shielding is arranged in two layers at a position of the second opening and includes a first cup wall, a second cup wall overlapped with the first cup wall successively from the inside to the outside, and a first gap formed between the first cup wall and the second cup wall. An end of the first opening is inserted into the first gap to connect with the cup shielding. The UV sterilization member is installed on a top end of the second cup wall and the waterproof transparent member is arranged on the second cup wall and formed below the UV sterilization member.

Wherein the first cup wall includes a first thread formed on its inner wall thereof and the cup body includes a second thread formed on an outer wall of the first opening to correspondingly engage with the first thread.

Wherein the length of the second cup wall extending along a longitudinal direction of the cup body towards the first opening is greater than that of the first cup wall extending along the longitudinal direction of the cup body towards the first opening, the second cup wall extending into the first receiving room.

Wherein the cup shielding further includes a main body with a hollow configuration and opening-setting in its two sides, a cover, and a frame tightly fixed in the second cup wall with a battery therein. The second opening is formed on one side of the main body and the first and second cup walls are arranged on the one side of the main body, the cover covered on the other side of the main body away from the second opening, and all the cover, the main body and the frame are cooperatively surrounded to form the second receiving room. The UV PCB is mounted on the other side of the main body adjacent to the cover, the UV light source mounted on the second cup wall and formed on a lower end of the frame to abut against the frame, the waterproof transparent member mounted on the second cup wall and formed on a bottom end of the UV light source to abut against the bottom end of the UV light source.

Wherein the frame further includes an installing plate formed on its upper portion thereon and including a connecting hole thereof, the main body including a plurality of supporting steps arranged at intervals for supporting the UV PCB, the installing plate abutting against a top portion of a connecting stud which is formed on the supporting step to connect the connecting stud and the connecting hole via screws.

Wherein the UV light source includes a UV light panel abutting against the lower end of the frame and including at least one UV LED formed thereon, and a reflector connected to the UV light panel and including a narrow portion abutting against the bottom of the UV light panel and surrounding the at least one UV LED therein, and a wide portion opposite to the narrow portion. The waterproof transparent member includes a UV transparent plate with high transmittance with its upper portion abutting against the wide portion, and a sealing ring surrounding the periphery of the UV transparent plate and interferently fitted with the inner wall of the second cup wall. The main body further includes a waterproof step protruding out from the inner wall of a lower portion of the second cup wall and abutting against the bottom of the UV transparent plate.

Wherein the main body further includes a waterproof groove formed on the inner wall of the lower portion of the second cup wall for receiving a waterproof sealing sleeve therein.

Wherein a plurality of supporting ribs for supporting the UV PCB is arranged at intervals on the circumferential of the main body where the UV PCB is installed.

Wherein the main body further includes a concave portion with a Micro USB port thereof, a silicone ring covered on the concave portion for sealing the Micro USB port, and a Micro USB connector inserted into the Micro USB port to electrically connect with the UV PCB.

Wherein the Micro USB port includes a cap arranged on a position where the silicone ring is installed, and the cap is rotatably connected to the silicone ring.

Wherein the cover further includes a window formed on its upper end thereof, and a button hole formed adjacent to the window and including a key formed thereon for connecting to the UV PCB, a window transparent plate covered on the window and including a display screen formed on the bottom thereof to connect to the UV PCB.

Wherein the UV sterilization cup further includes a filter used in conjunction with the first opening of the cup body.

Wherein the filter includes a housing with a hollow configuration and opening-setting in its two ends, and a filtering core received in the housing. The housing is arranged in two layers at one end adjacent to the end of the first opening and includes a third cup wall, a fourth cup wall overlapped with the third cup wall successively from the inside to the outside, and a second gap formed between the third cup wall and the fourth cup wall. An opposite end of the first opening adjacent to the cup body is inserted into the second gap to connect with the housing, and the filtering core is installed on the fourth cup wall.

Wherein the filtering core includes at least one of an activated carbon filtering core and a PP cotton+ activated carbon filtering core.

Wherein the UV generating circuit includes a main control chip, a step-up driving circuit, a charge and discharge management circuit, a voltage-regulating circuit, a display driving circuit and a keying circuit respectively connected to the main control chip; the main control chip configured to generate a UV generating signal and then drive the UV light source to emit ultraviolet ray according to the UV generating signal amplified by the step-up driving circuit; the charge and discharge management circuit configured to receive a control signal of the main control chip to charge or discharge a battery; the voltage-regulating circuit configured to stabilize the voltage processed by the charge and discharge management circuit and to provide a stabilization power supply for the main control chip; the display driving circuit configured to receive signals of the main control chip and send the signals to a display screen; and the keying circuit configured to receive an input signal from users and then send it to the main control chip.

Wherein the charge and discharge management circuit includes a charge and discharge management chip electrically connected to the main control chip and connected with a connecting port of the battery, and a Micro USB connector circuit connected to the charge and discharge management chip; the charge and discharge management chip configured to receive the control signal of the main control chip and input electronic energy to the connecting port of the battery via the Micro USB connector circuit to charge the battery or output electronic energy to the Micro USB connector circuit via the connecting port of the battery to discharge the battery.

Wherein the display driving circuit is configured to drive the display screen to at least display the temperature of fluid that is received in the UV sterilization cup, the power level, the charging indicator and the sterilization timing status.

Wherein the step-up driving circuit includes a power amplifying circuit and a step-up constant current circuit with a step-up constant current chip therein, and the voltage-regulating circuit includes a voltage regulator therein. The step-up constant current chip is an AL8822-type chip, the main control chip is a HT66F019 single chip microcomputer, the voltage regulator is a 7533-type chip and the charge and discharge management chip is an IP5306-type chip.

The present disclosure provides the advantages as below.

The structure of the present disclosure can some advantageous shown below: 1). It can achieve a good sterilization effect with 99.9% by the UV light source to sterilize water and have a compact structure; 2). It can have a high circuit integration structure to greatly reduce the volume of the cup shielding and conveniently carry it; 3). Water fetched in outdoors can be first filtered by the filter with an activated carbon filtering layer or a PP cotton+ activated carbon filtering layer, and then can be sterilized by covering the cup shielding with a UV sterilization member for sterilization treatment; 4). The cup body is preferably made of stainless steel, but not limited to stainless steel and is vacuumed therein so that it has the function of heat preservation; 5). The cup body has a uniform caliber so that cups with different volume can match with a same cup shielding; 6). The cup shielding is made of environment-friendly food grade material via ultrasonic welding technology so that it is safe and reliable, at the same time, it is made of IP66-class waterproof dust so that its surface can be directly washed with water; there is also a large-capacity lithium battery set in the cup shielding, which can be charged by a Micro USB port via only a common charging data line: and a display screen set on the cup shielding, which can at least display its current temperature and power level, and its charging indicator light; 7). Water fetched in outdoors can reach the standard of healthy drinking water that it is first filtered by the filter and then sterilized by the UV light source.

BRIEF DESCRIPTION OF THE DRAWINGS

Many aspects of the embodiments can be better understood with reference to the following drawings. The components in the drawings are not necessarily drawn to scale, the emphasis instead being placed upon clearly illustrating the principles of the embodiments. Moreover, in the drawings, like reference numerals designate corresponding parts throughout the several views.

Figure 1:
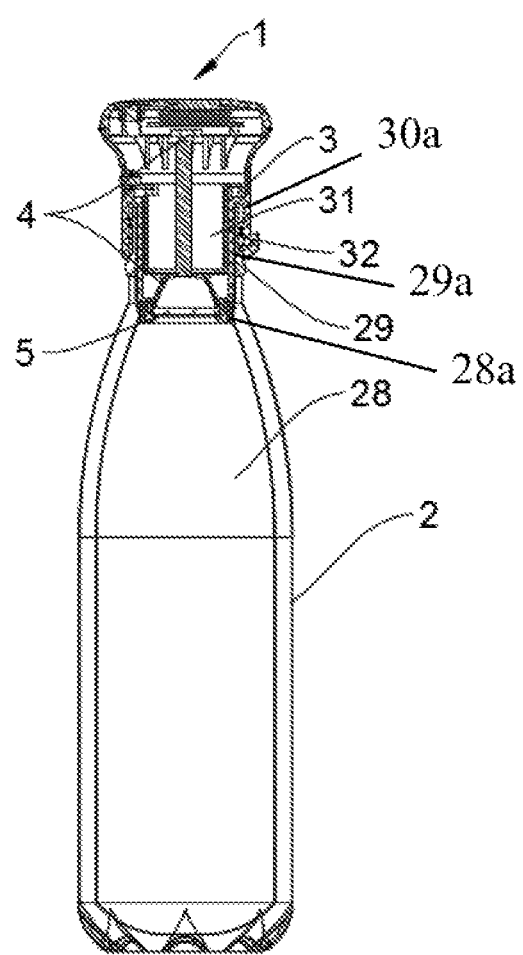
FIG. 1 is a schematic view of the UV sterilization cup in accordance with an exemplary embodiment.
Figure 2:
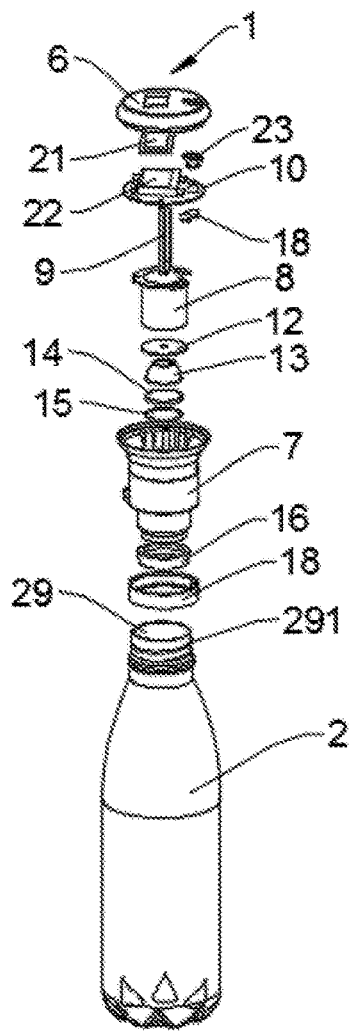
FIG. 2 is an exploded, schematic view of the UV sterilization cup of FIG. 1.

The element labels according to the exemplary embodiment of the present disclosure shown as below:

UV sterilization cup 1, cup body 2, first receiving room 28, first opening 29, end 29a, second thread 291, cup shielding 3, wall 30a, second receiving room 31, one end 31a, the other end 31b, second opening 32, UV sterilization member 4, waterproof transparent member 5, cover 6, upper end 6a, window 61, button hole 62, main body 7, side 7a, firs wall 71, second wall 72, top end 72a, waterproof step 721, waterproof groove 722, first gap 73, first thread 74, supporting rib 75, cancave portion 76, supporting step 77, connecting stud 771, top portion 771a, frame 8, upper portion 8a, lower end 8b, installing plate 81, connecting hole 82, battery 9, UV PCB 10, UV light source 11, bottom end 11a, UV light panel 12, reflector 13, narrow portion 131, wide portion 132, UV transparent plate 14, sealing ring 15, waterproof sealing sleeve 16, Micro USB port 17, Micro USB connector 18, silicone ring 19, cap 20, window transparent plate 21, display screen 22, J1, key 23, filter 24, housing 25, third cup wall 251, fourth cup wall 252, second gap 253, filtering core 26, UV generating circuit 100, main control chip A, U3, step-up driving circuit B, power amplifying circuit B1, step-up constant current circuit B2, step-up constant current chip U1, charge and discharge management circuit C, charge and discharge management chip C1, U2, Micro USB connector circuit C2, connecting port C3, voltage-regulating circuit D, voltage regulator U4, display driving circuit E, keying circuit F, first P-MOS Q1, second P-MOS Q2, third P-MOS Q3, fourth NPN-type triode Q4, first resistor R1, seventh resistor R7, key-switch K1, eighth resistor R8, eleventh resistor R11, twelfth resistor R12, fourteenth resistor R14, sixteenth resistor R16, seventeenth resistor R17, eighteenth resistor R18, nineteenth resistor R19, twentieth resistor R20, twenty-first resistor R21, twenty-second resistor R22, diode D3, first inductor L1, second inductor L2, seventh capacitor C7, ninth capacitor C9, tenth capacitor C10, thirteenth capacitor C13, seventeenth capacitor C17.

DETAILED DESCRIPTION

The disclosure is illustrated by way of example and not by way of limitation in the figures of the accompanying drawings, in which like reference numerals indicate similar elements.

Referring to FIGS. 1-4, the UV sterilization cup 1 in accordance with an exemplary embodiment is provided. The UV sterilization cup 1 includes a cup body 2, a cup shielding 3 connected to the cup body 2, a UV sterilization member 4 received in the cup shielding 3, and a waterproof transparent member 5 mounted on the bottom of the cup shielding 3 and connected to the UV sterilization member 4. The cup body 2 includes a first receiving room 28 with a first opening 29 being formed on its portion 28a adjacent to the cup shielding 3. The cup shielding 3 includes a second receiving room 31 with a second opening 32 being formed on its one end 31a adjacent to the cup body 2 and connected to the first opening 29. The UV sterilization member 4 is received in the second receiving room 31 to emit ultraviolet ray and the waterproof transparent member 5 is received in the cup shielding 3 and adjacent to the first receiving room 28 for sealing the UV sterilization member 4 to block connection between the first receiving room 28 and the second receiving room 31. The waterproof transparent member 5 is configured to transmit the ultraviolet ray emitted from the UV sterilization member 4 into the first receiving room 28. The UV sterilization member 4 includes a UV PCB 10 installed in the other end 31b of the second receiving room 31 far away from the second opening 32, and a UV light source 11 electrically connected to a UV generating circuit 100 of the UV PCB 10 and installed in the one end 31a of the second receiving room 31 adjacent to the second opening 32. The waterproof transparent member 5 is also mounted on a bottom end 11a of the UV light source 11 to abut against the bottom end 11a of the UV light source 11.

In an exemplary embodiment of the present disclosure. The first receiving room 28 is provided for holding drinking water or other liquids and the cup shielding 3 is placed on the cup body 2, and then a through-hole circuit of the UV sterilization member 4 received in the cup shielding 3 is turned on so that the UV sterilization member 4 can generate ultraviolet ray, which passes through the waterproof transparent member 5 and then shoots to the first receiving room 28 to sterilize the water contained in the first receiving room 28. The waterproof transparent member 5 is provided to prevent the liquid in the first receiving room 28 from flowing into the second receiving room 31 to damage the UV sterilization member 4 due to short-circuit and other phenomena.

In an exemplary embodiment of the present disclosure, the UV sterilization member 4 is arranged in the cup shielding 3 so that the ultraviolet ray generated by the UV sterilization member 4 can efficiently sterilize the liquid in the cup body 2, thereby the sterilization efficiency can reach about 99.9%.

Figure 3:
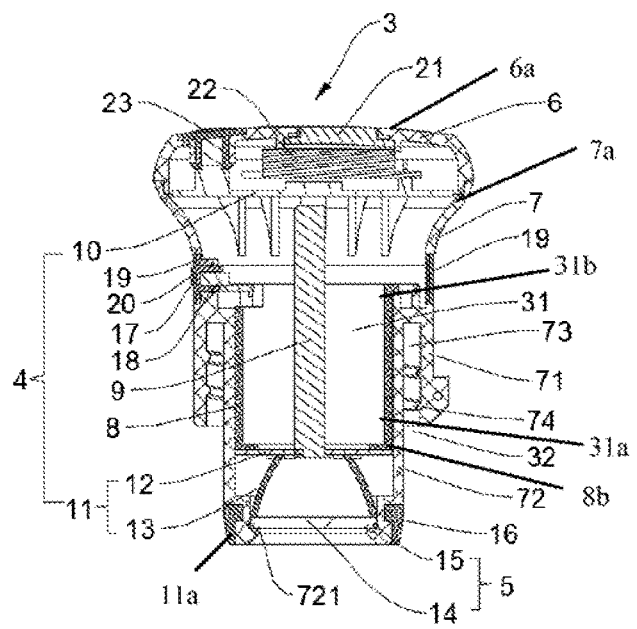
FIG. 3 is a cross sectional view of a cup shielding of the UV sterilization cup of FIG. 1.

Specifically, referring to FIG. 3, a wall 30a of the cup shielding 3 is arranged in two layers at a position of the second opening 32 and includes a first cup wall 71, a second cup wall 72 overlapped with the first cup wall 71 successively from the inside to the outside, and a first gap 73 formed between the first cup wall 71 and the second cup wall 72. An end 29a of the first opening 29 is inserted into the first gap 73 to connect with the cup shielding 3. The UV sterilization member 4 is installed on a top end 72a of the second cup wall 72 and the waterproof transparent member 5 is arranged on the second cup wall 72 and formed below the UV sterilization member 4.

The wall 30a is arranged in two layers so that the second cup wall 72 can be inserted into the first receiving room 28 after the cup shielding 3 is covered on the cup body 2. In this way, the ultraviolet ray generated by the UV sterilization member 4 within the second cup wall 72 can be further transmitted from the waterproof transparent member 5 so that the distance between the ultraviolet ray and the water in the first receiving room 28 is more short, which can improve the sterilization efficiency of the ultraviolet ray.

As a means of connection, in an exemplary embodiment of the present disclosure, the first cup wall 71 includes a first thread 74 formed on its inner wall thereof, and the cup body 2 includes a second thread 291 formed on an outer wall of the first opening 29 to correspondingly engage with the first thread 74. In this way, the cup body 2 can be firmly connected with the cup shielding 3 via the thread connection way. It can be understood that the cup body 2 and the cup shielding 3 can be connected to each other via another way such as a plug-in connection way.

Preferably, the length of the second cup wall 72 extending along a longitudinal direction of the cup body 2 towards the first opening 29 is greater than that of the first cup wall 71 extending along the longitudinal direction of the cup body 2 towards the first opening 29, with the second cup wall 72 extending into the first receiving room 28. In this way, the second cup wall 72 can protrude from the cup shielding 3 so that it can directly extend into the first receiving room 28. Therefore, the ultraviolet ray emitted by the UV sterilization member 4 can be directly irradiated into the water within the first receiving room 28 after it is transmitted through the waterproof transparent member 5, which can reduce the loss of ultraviolet ray transmission process to further improve its sterilization efficiency.

Figure 4:
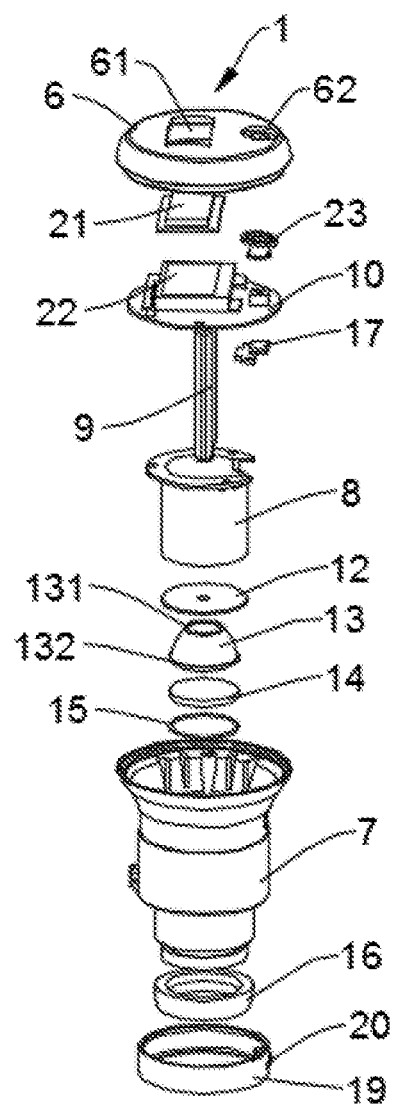
FIG. 4 is an exploded, schematic view of the cup shielding of the UV sterilization cup of FIG. 1.

Specifically, referring to FIG. 3 and FIG. 4, the cup shielding 3 further includes a main body 7 with a hollow configuration and opening-setting in its two sides, a cover 6, and a frame 8 tightly fixed in the second cup wall 72 with a battery 9 therein. The second opening 32 is formed on one side of the main body 7 and the first and second cup walls 71, 72 are arranged on the one side of the main body 7, and the cover 6 is covered on the other side 7a of the main body 7 far away from the second opening 32. All the cover 6, the main body 7 and the frame 8 are cooperatively surrounded to form the second receiving room 31.

The UV PCB 10 is mounted on the other side 7a of the main body 7 adjacent to the cover 6, and the UV light source 11 is mounted on the second cup wall 72 and formed on a lower end 8b of the frame 8 to abut against the frame 8. The waterproof transparent member 5 is mounted on the second cup wall 72 and formed on the bottom end 11a of the UV light source 11 to abut against the bottom end 11a of the UV light source 11. In this way, the UV light source 11 is located between the frame 8 and the waterproof transparent member 5 and is tightly held by them. The frame 8 is fixed with the second cup wall 72 to support the UV light source 11 and the waterproof transparent member 5, thereby the UV light source 11 and the waterproof transparent member 5 can be effectively prevented from loosening during using them. At the same time, the frame 8 is a hollow structure to conveniently receive the battery 9 therein.

Figure 5:
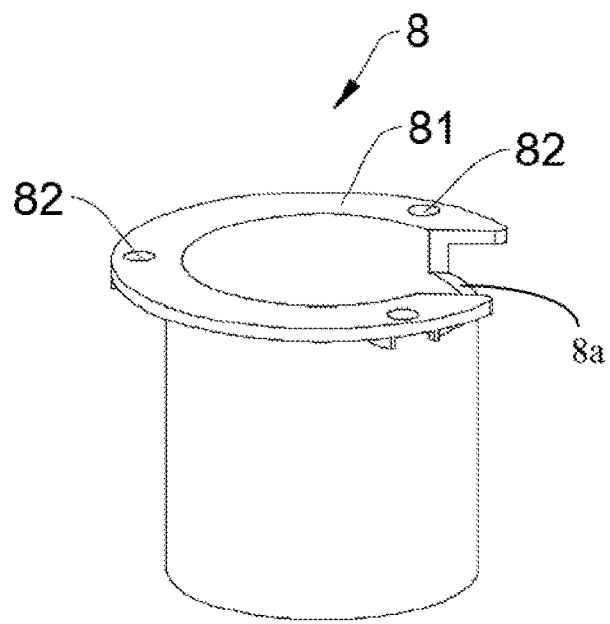
FIG. 5 is a schematic view of a frame of the UV sterilization cup of FIG. 1.
Figure 6:
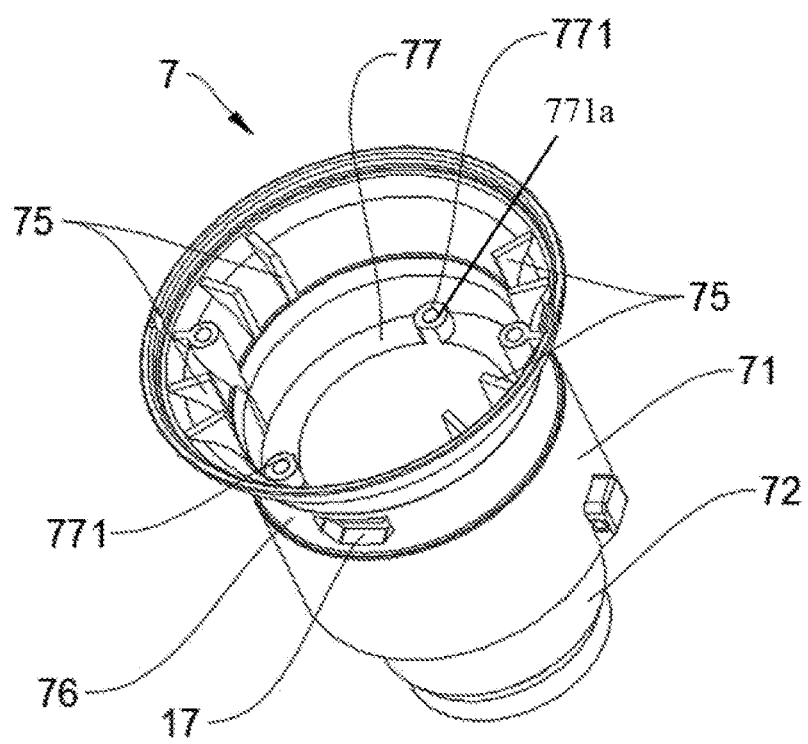
FIG. 6 is a schematic view of a main body of the cup shielding of the UV sterilization cup of FIG. 1.

Referring to FIG. 5 and FIG. 6, the frame 8 further includes an installing plate 81 formed on the upper portion 8a thereon and including a connecting hole 82 thereof, and the main body 7 includes a plurality of supporting steps 77 arranged at intervals for supporting the UV PCB 10. The installing plate 81 is abutted against a top portion 771a of a connecting stud 771 which is formed on the supporting step 77 to connect the connecting stud 771 and the connecting hole 82 via screws. In this way, the frame 8 can be firmly fixed with the main body 7 for supporting the UV light source 11, the waterproof transparent member 5 and the battery 9. At the same time, the installation of the UV PCB 10 in the main body 7 can't be interfered.

Figure 7:
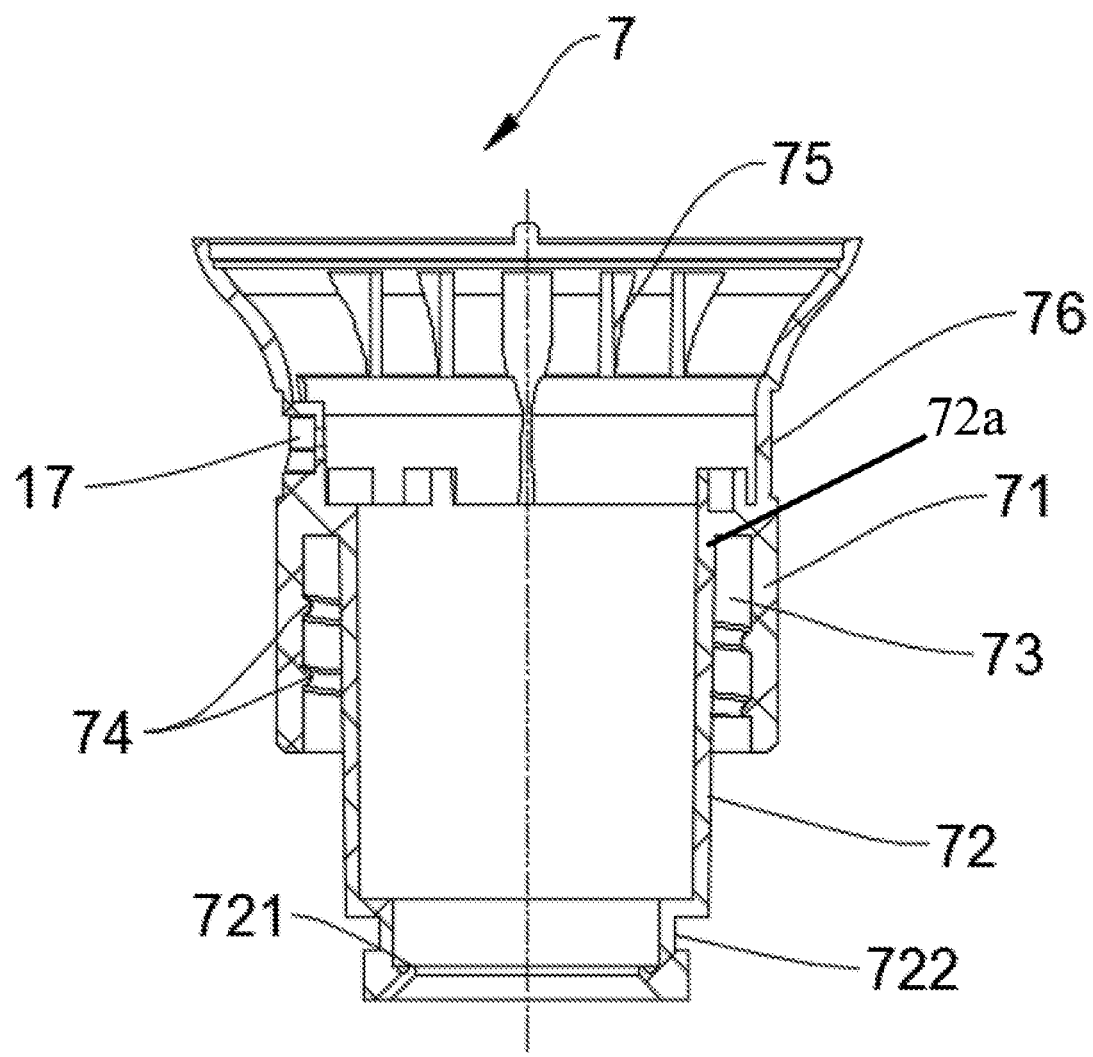
FIG. 7 is a cross sectional view of the main body of the UV sterilization cup of FIG. 1.

Referring to FIGS. 3-4 and FIG. 7, the UV light source 11 includes a UV light panel 12 abutting against the lower end 8b of the frame 8 and including at least one UV LED formed thereon, and a reflector 13 connected to the UV light panel 12 and including a narrow portion 131 abutting against the bottom of the UV light panel 12 and surrounding the at least one UV LED therein, and a wide portion 132 opposite to the narrow portion 131.

The waterproof transparent member 5 includes a UV transparent plate 14 with high transmittance with its upper portion abutting against the wide portion 132, and a sealing ring 15 surrounding the periphery of the UV transparent plate 14 and interferently fitted with the inner wall of the second cup wall 72. The main body 7 further includes a waterproof step 721 protruding out from the inner wall of a lower portion of the second cup wall 72 and abutting against the bottom of the UV transparent plate 14. It can be seen that the UV transparent plate 14 is tightly abutted against the waterproof step 721 so as to successively support the reflector 13 and the UV light panel 12. At the same time, the UV transparent plate 14 can effectively transmit the ultraviolet ray emitted from the at least one UV LED arranged on the UW light panel 12 to further reduce the transmission loss of the ultraviolet ray. The UV transparent plate 14 is configured to have a good light transmission effect, which can greatly reduce the loss of the ultraviolet ray to further improve sterilization efficiency of the ultraviolet ray.

The UV LED of the present disclosure is an LED light which can generate ultraviolet ray according to circuit controls, and can be determined according to the volume of the cup body 2. Two or three UV LEDs can be set when the volume of the cup body 2 is great. For the cup body 2 with different capacity, different amount of the UV LEDs can be used to ensure the maximum bactericidal effect to achieve a reasonable usage of resources without waste. At the same time, lighting time of the UV LED can be controlled by controlling its circuits, thereby 99.9% bacteria can be killed within its working time.

Referring to FIG. 3 and FIG. 7, the main body 7 further includes a waterproof groove 722 formed on the inner wall of the lower portion of the second cup wall 72 for receiving a waterproof sealing sleeve 16 therein. In this way, the water received in the cup body 2 can be prevented from leaking out after the cup shielding 3 is connected with the cup body 2.

Preferably, a plurality of supporting ribs 75 for supporting the UV PCB 10 is arranged at intervals on the circumferential of the main body 7 where the UV PCB 10 is installed. The supporting rib 75 is provided to support the UV PCB 10 stably, and be beneficial to heat dissipation of the UV PCB 10.

Preferably, combining FIG. 3 and FIG. 7, the main body 7 further includes a concave portion 76 with a Micro USB port 17 thereof, a silicone ring 19 covered on the concave portion 76 for sealing the Micro USB port 17, and a Micro USB connector 18 inserted into the Micro USB port 17 to electrically connect with the UV PCB 10. The Micro USB port 17 is configured to connect an external power supply to supply power for the UV PCB 10 and charge the battery 9, and the silicone ring 19 is waterproof and protective for the Micro USB connector 18 received in the Micro USB port 17.

Furthermore, the Micro USB port 17 includes a cap 20 arranged on a position where the silicone ring 19 is installed, and the cap 20 is rotatably connected to the silicone ring 19. The cap 20 is provided for conveniently opening or closing the Micro USB port 17.

The cover 6 further includes a window 61 formed on its upper end 6a thereof and a button hole 62 formed adjacent to the window 61. A window transparent plate 21 is covered on the window 61 and includes a display screen 22 formed on the bottom thereof to connect to the UV PCB 10, and a key 23 is formed on the button hole 62 for connecting to the UV PCB 10. In an exemplary embodiment of the present disclosure, the display screen 22 is provided for at least displaying the temperature of fluid that is received in the UV sterilization cup 1, the power level, the charging indicator and the sterilization timing status to improve user's experience. While, the key 23 is provided for controlling sterilization on or off and sterilization time of the UV sterilization cup 1.

Figure 8:
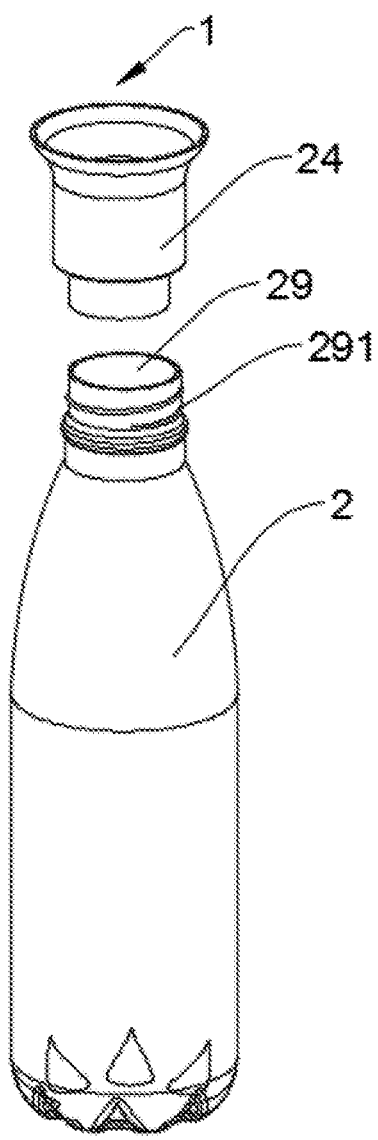
FIG. 8 is a schematic view of a filter and a cup body of the UV sterilization cup of FIG. 1.
Figure 9:
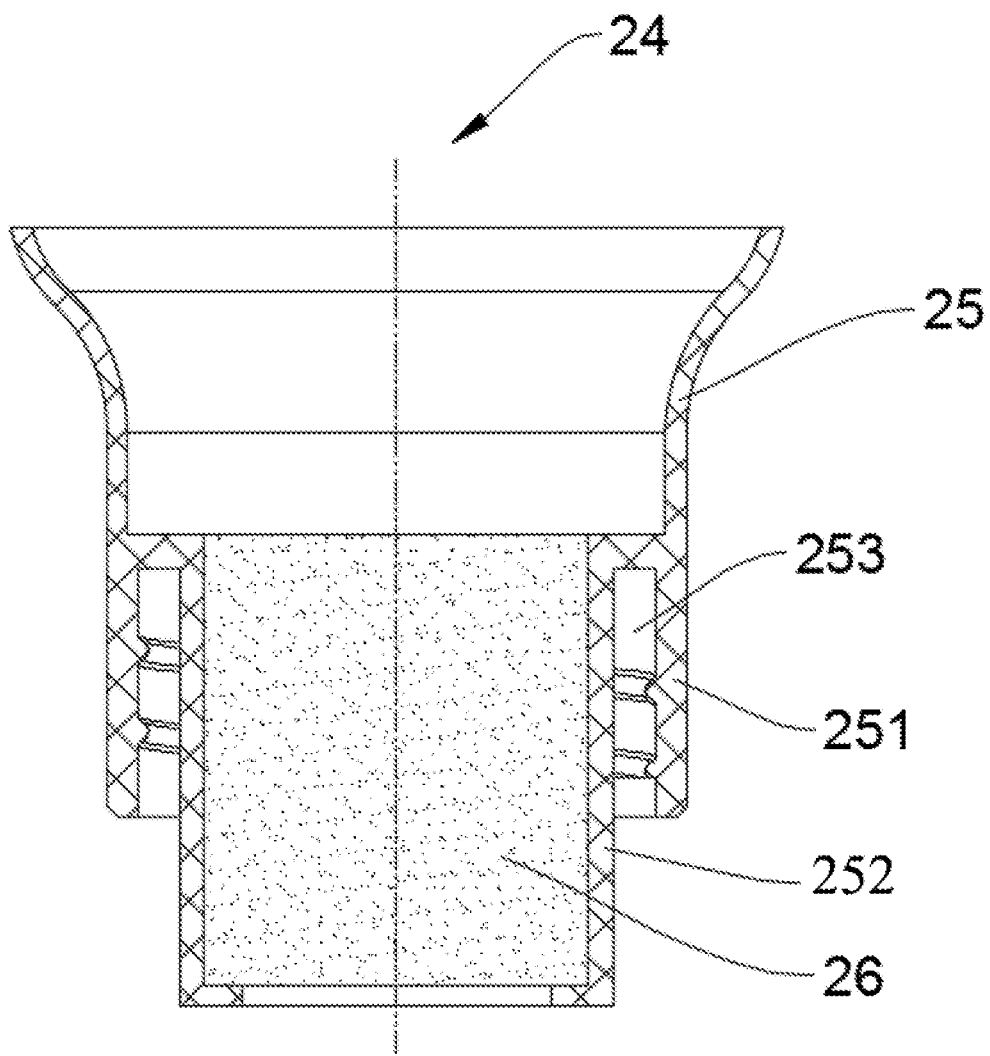
FIG. 9 is a cross sectional view of the filter of the UV sterilization cup of FIG. 1.

Referring to FIG. 8 and FIG. 9, the UV sterilization cup 1 further includes a filter 24 used in conjunction with the first opening 29 of the cup body 2. The filter 24 is provided for first filtering water and then sterilizing the water to ensure the water reach the standard of healthy drinking water when the water is fetched in outdoors.

Specifically, the filter 24 includes a housing 25 with a hollow configuration and opening-setting in its two ends, and a filtering core 26 received in the housing 25. The housing 25 is arranged in two layers at its one end adjacent to the end 29a of the first opening 29 and includes a third cup wall 251, a fourth cup wall 252 overlapped with the third cup wall 251 successively from the inside to the outside, and a second gap 253 formed between the third cup wall 251 and the fourth cup wall 252. An opposite end of the first opening 29 adjacent to the cup body 2 is inserted into the second gap 253 to connect with the housing 25, and the filtering core 26 is installed on the fourth cup wall 252. The upper of the housing 25 is hollow for water connection, and the filtering core 26 is received in an empty middle part of the housing 25.

Preferably the filtering core 26 includes at least one of an activated carbon filtering core and a PP cotton+ activated carbon filtering core.

It is well known that substances in outdoor water can be classified according to particle size therein into suspended substances, colloidal substances, dissolved substances, ions and molecules, organic substances and water molecules themselves.

1. The suspended substance with its particle about 10-4 mm or more in its diameter is visible to naked eyes. The particle is mainly consisted of sediment, clay, protozoa, algae, bacteria, viruses and macromolecule organic substances which are often suspended in flow water, so that phenomenon of turbid water is also caused by such substances. The suspended substance is a main source of turbidity, chromaticity and smell.

2. The colloidal substance with its particle between 10-4 mm and 10-6 mm in its diameter is collections of many molecules and ions. The inorganic mineral colloids in natural water are mainly compounds containing iron, aluminum and silicon. The organic colloid substance is mainly humus produced by the decomposition and decay of animals and plants. Surface of the colloid substance has a large adsorption capacity because it has a large surface area per unit volume.

3. The dissolved substance with its particle between 10-4 mm in its diameter is mainly dissolved in water in a presence of a low molecular solution of salt ions and gases.

4. The organic substance in water is mainly compounds containing humic acid and fulvic acid, and pollutants such as domestic sewage and industrial wastewater. It contains animal and vegetable fibers, oils, grains, dyes, organic materials and so on. A common feature of the organic substance in water is that it needs to be oxidized and decomposed, which requires the consumption of dissolved oxygen in water, thereby resulting in the lack of oxygen in water. At the same time, putrid fermentation can be occurred, thereby leading to bacteria breed, deterioration of water quality and destruction of water. So, the organic substance is a main cause of water pollution.

Activated carbon includes a plurality of capillary pores therein connected to each other so that it has a great surface area. According to the test, it has a surface area of 500-1000 $m^2$ in one gram activated carbon. The activated carbon used for filtration is granular with its particle diameter generally about 1-4 mm so that these capillary pores can play as an adsorption role. In this way, the activated carbon dechlorination isn't completely caused by physical adsorption, it also has a catalytic effect, so that the residual chlorine is further converted into carbon compounds with its chemical equation: $Cl_2+H_2O=HCl+HOCl$, $HOCl=HCl+[O]$, the activated carbon: $C+[O]=CO$, $C+2[O]=CO2$. So, the activated carbon can't have a problem of adsorption saturation in the whole adsorption dechlorination process, but only losing a small amount of carbon, thereby a very good filtration effect can be obtained.

The PP cotton+activated carbon filtering core is divided into two layers that the upper layer is PP cotton filtration and the lower layer is activated carbon filtration.

Figure 10:
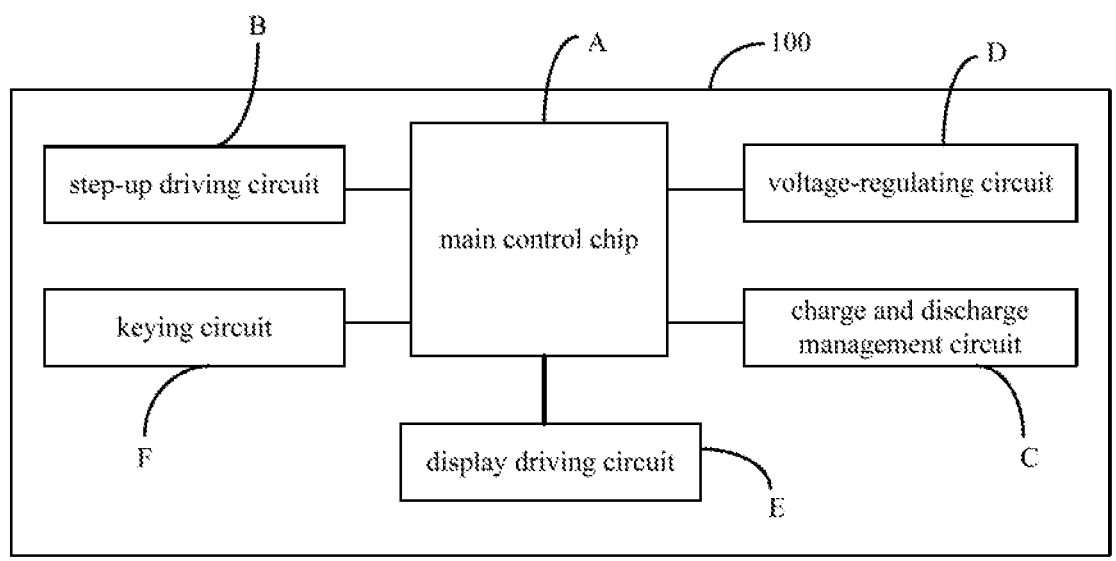
FIG. 10 is a circuit diagram of a UV generating circuit of the UV sterilization cup of FIG. 1.
Figure 11:
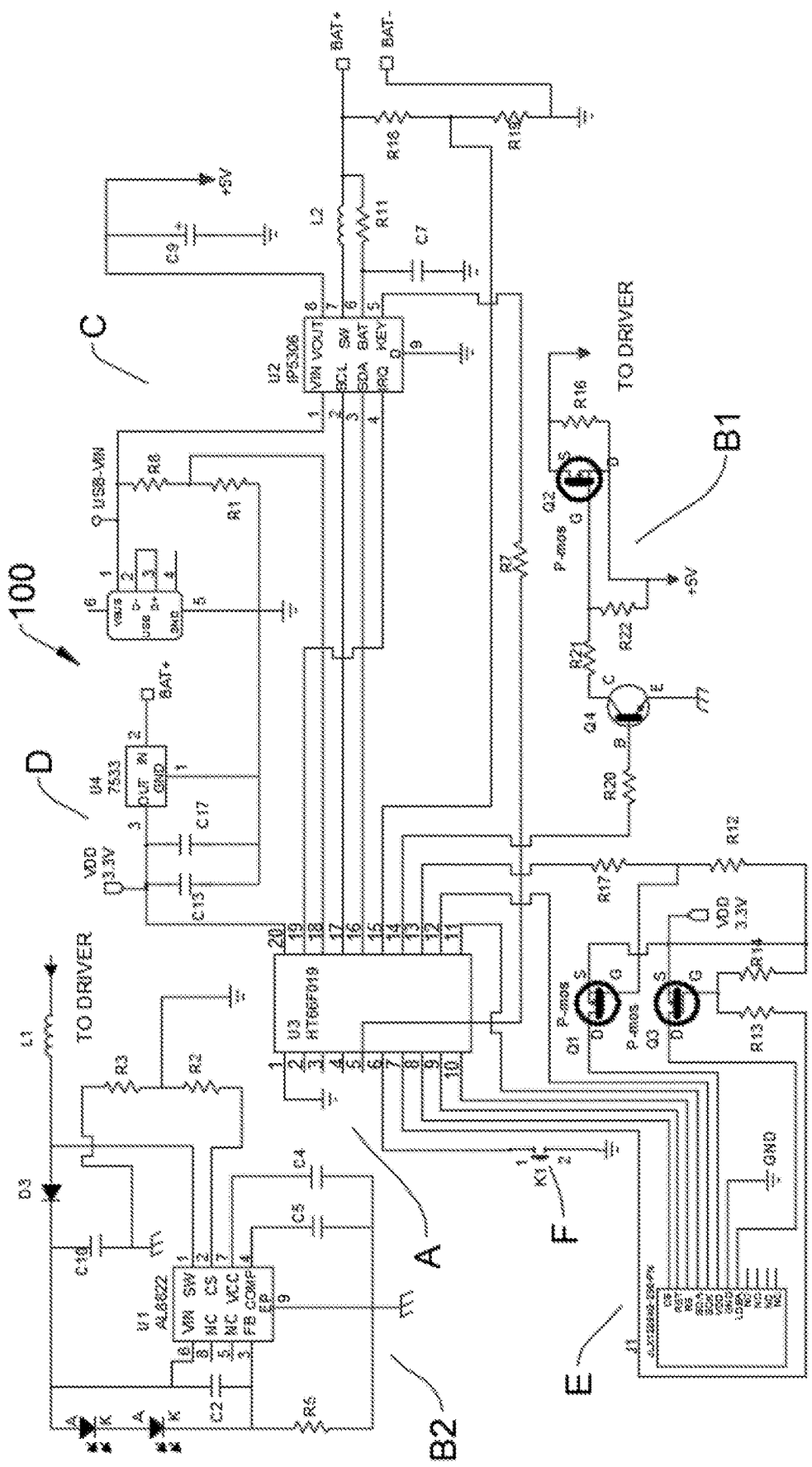
FIG. 11 is a circuit view of the UV generating circuit of the UV sterilization cup of FIG. 1.
Figure 12:
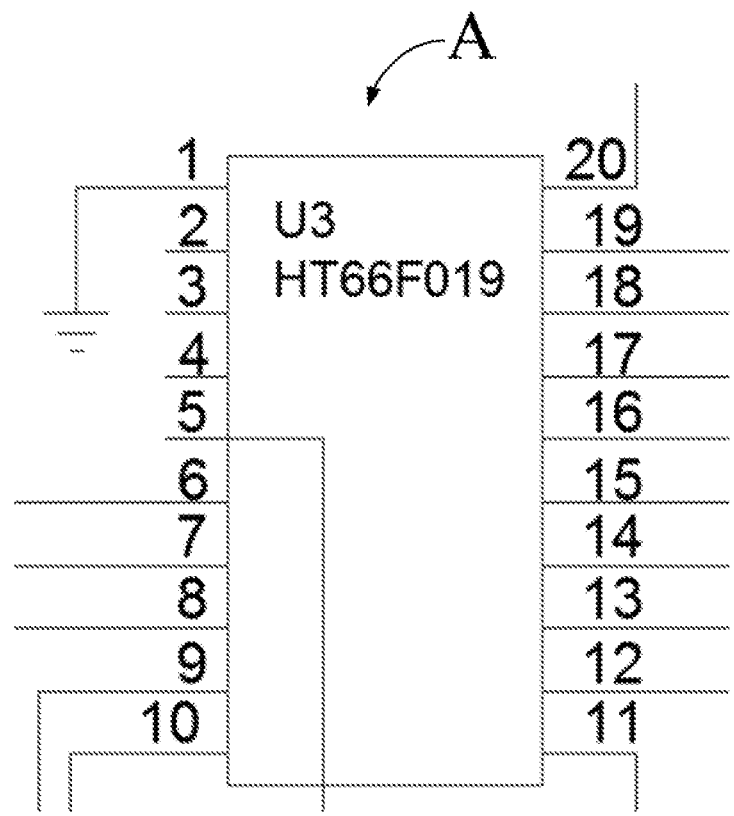
FIG. 12 is a circuit enlargement diagram of a main control chip A of the UV generating circuit of FIG. 10.
Figure 13:
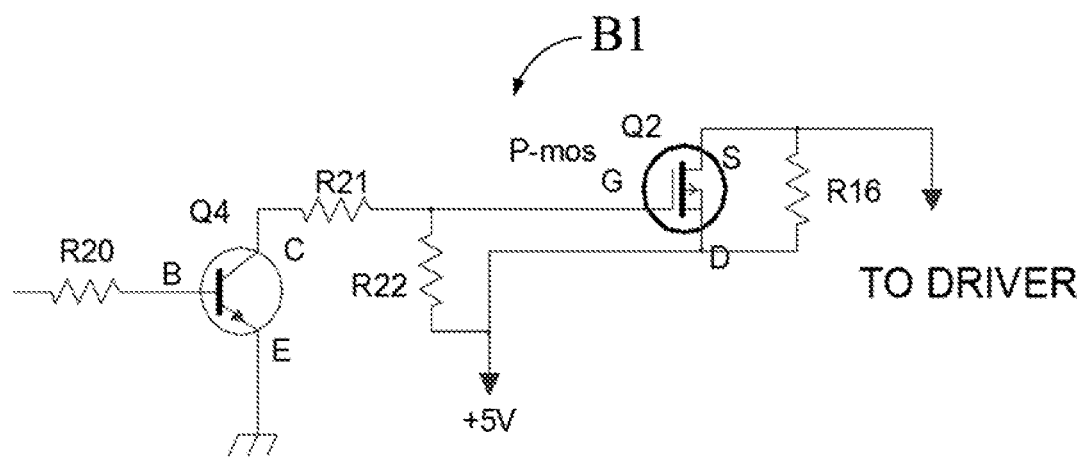
FIG. 13 is a circuit enlargement diagram of a power amplifying circuit within a step-up driving circuit of the UV generating circuit of FIG. 10.
Figure 14:
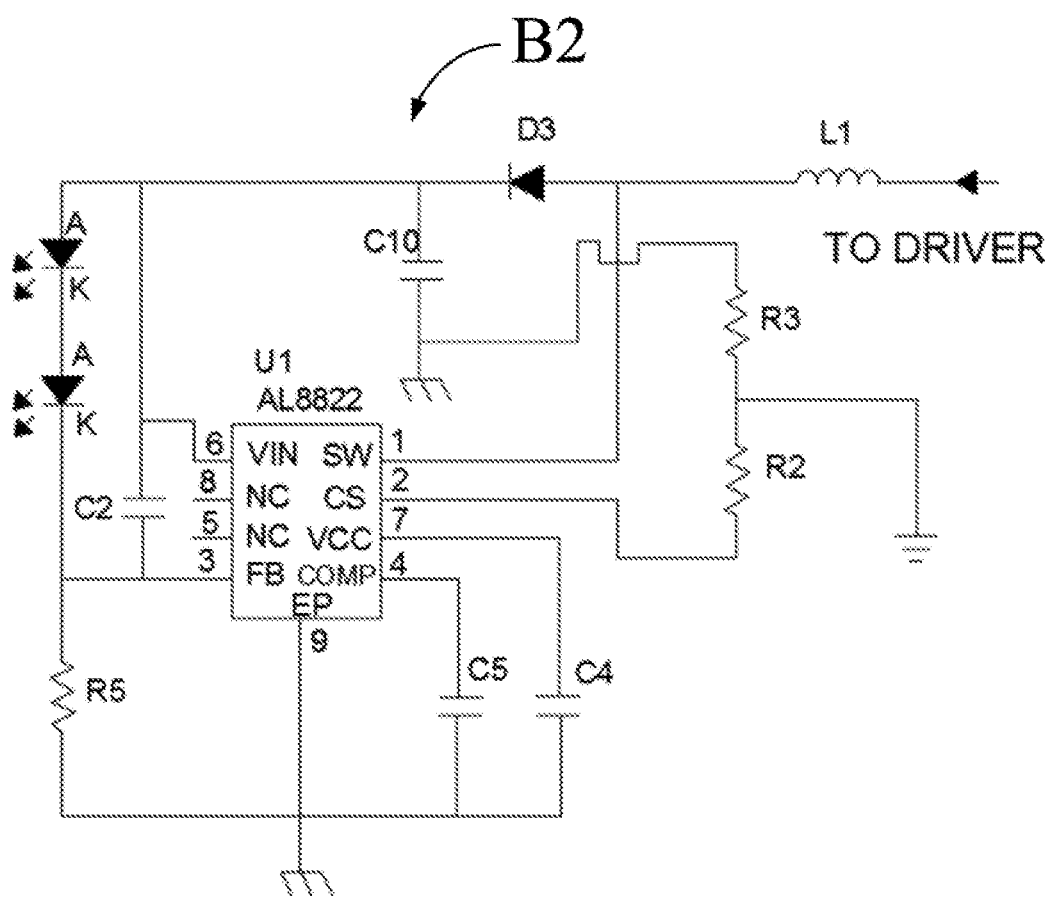
FIG. 14 is a circuit enlargement diagram of a step-up constant current circuit within the step-up driving circuit of the UV generating circuit of FIG. 10.
Figure 15:
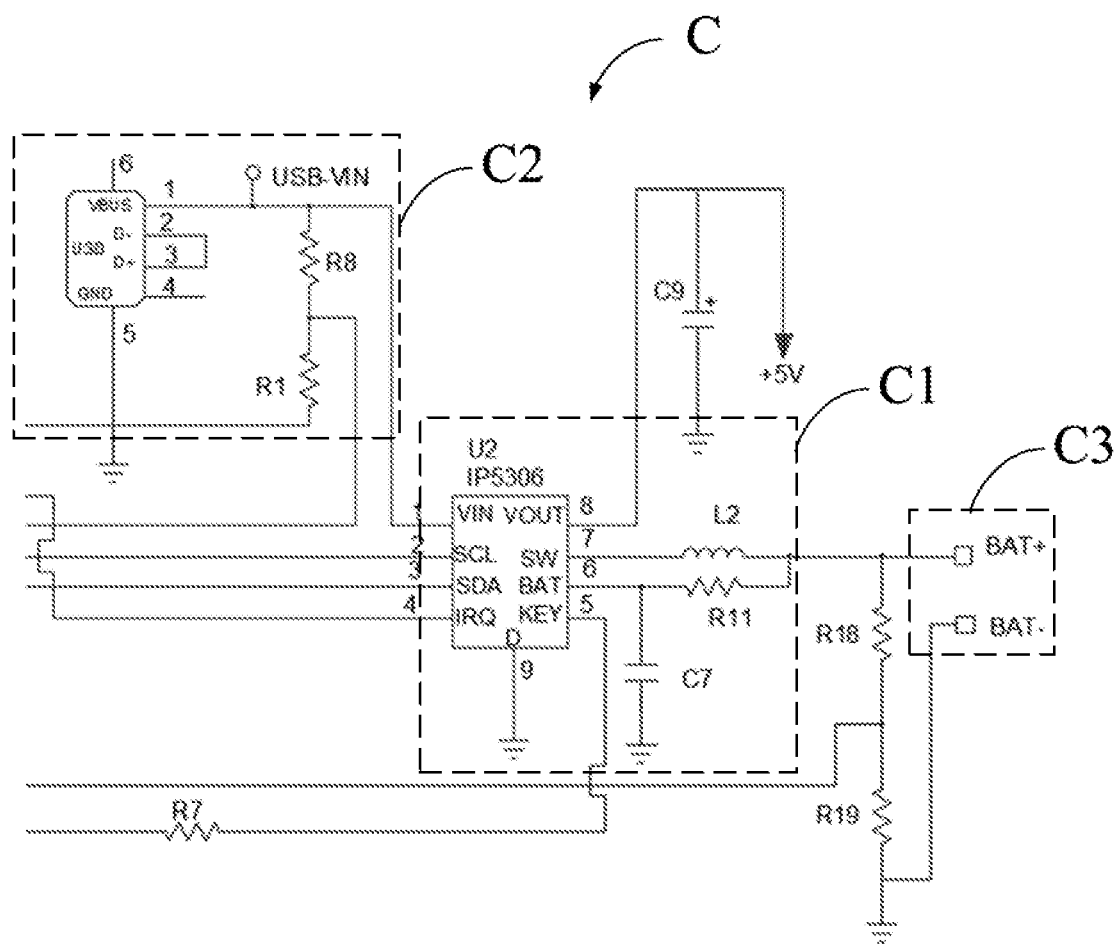
FIG. 15 is a circuit enlargement diagram of a charge and discharge management circuit of the UV generating circuit of FIG. 10.
Figure 16:
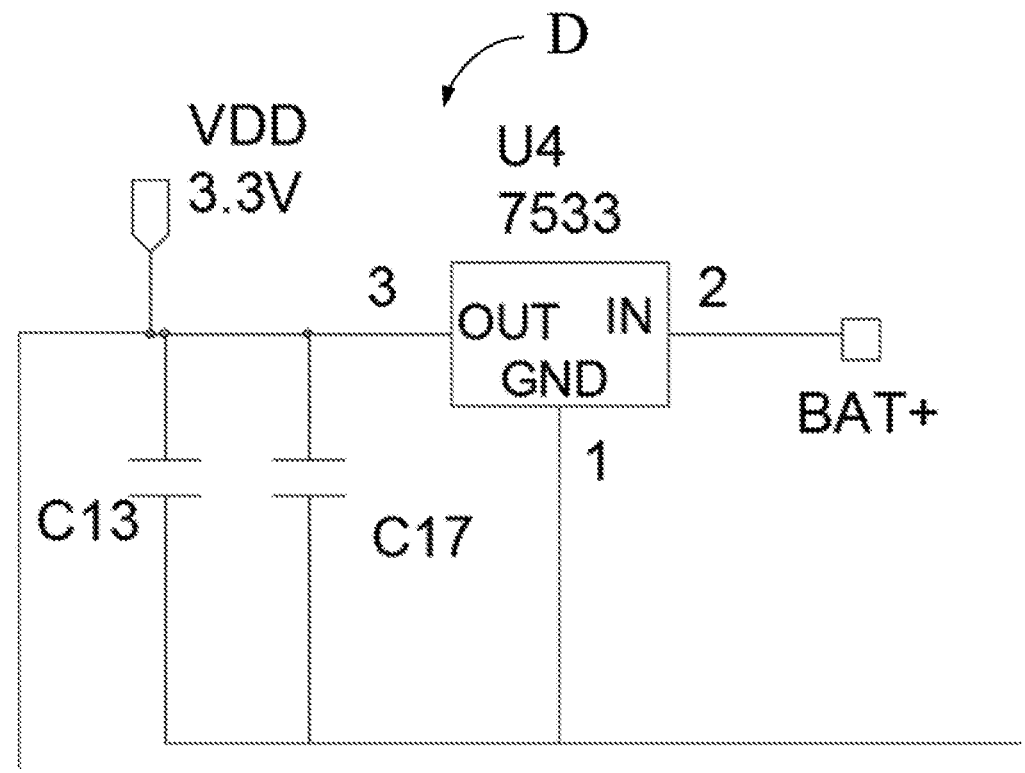
FIG. 16 is a circuit enlargement diagram of a voltage regulating circuit of the UV generating circuit of FIG. 10.
Figure 17:
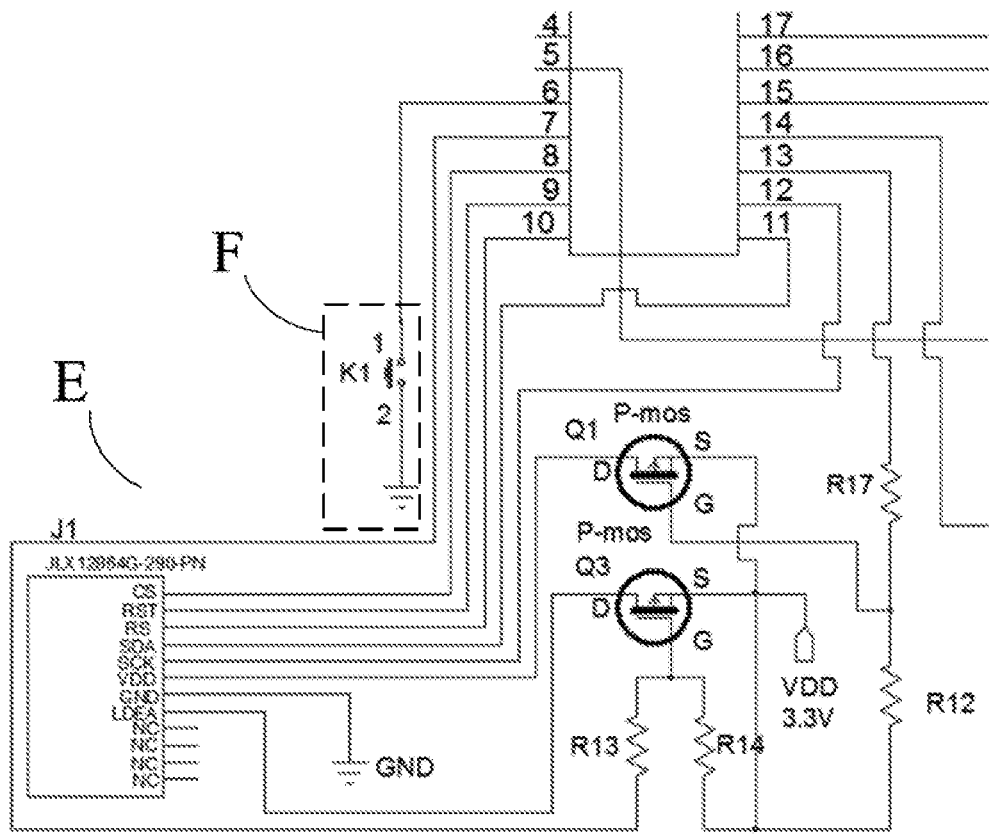
FIG. 17 is a circuit enlargement diagram of a display driving circuit and a keying circuit of the UV generating circuit of FIG. 10.

Referring to FIG. 10 and FIG. 11, the UV PCB 10 includes the UV generating circuit 100 which includes a main control chip A, a step-up driving circuit B, a charge and discharge management circuit C, a voltage-regulating circuit D, a display driving circuit E and a keying circuit F connected to the main control chip A, respectively. The main control chip A is configured to generate a UV generating signal and then drive the UV light source 11 to emit ultraviolet ray according to the UV generating signal amplified by the step-up driving circuit B. The charge and discharge management circuit C is configured to receive a control signal of the main control chip A to charge or discharge the battery 9. The voltage-regulating circuit D is configured to stabilize the voltage processed by the charge and discharge management circuit C and to provide a stabilization power supply for the main control chip A. The display driving circuit E is configured to receive signals of the main control chip A and send the signals to the display screen 22. The keying circuit F is configured to receive an input signal from users and then send it to the main control chip A.

Preferably, the display driving circuit E is configured to drive the display screen 22 to at least display the temperature of fluid that is received in the UV sterilization cup 1, the power level, the charging indicator and the sterilization timing status.

Preferably, the charge and discharge management circuit C includes a charge and discharge management chip C1 electrically connected to the main control chip A and connected with a connecting port C3 of the battery 9, and a Micro USB connector circuit C2 connected to the charge and discharge management chip C1. The charge and discharge management chip C1 is configured to receive the control signal of the main control chip A and input electronic energy to the connecting port C3 of the battery 9 via the Micro USB connector circuit C2 to charge the battery 9 or output electronic energy to the Micro USB connector circuit C2 via the connecting port C3 of the battery 9 to discharge the battery 9.

Referring to FIGS. 11-17, specific circuits are shown. The step-up driving circuit B includes a power amplifying circuit B1 and a step-up constant current circuit B2 with a step-up constant current chip U1 therein, and the voltage-regulating circuit D includes a voltage regulator U4 therein. In an exemplary embodiment of the present disclosure, the step-up constant current chip U1 is an AL8822-type chip, the main control chip A is a HT66F019 single chip microcomputer, the voltage regulator U4 is a 7533-type chip and the charge and discharge management chip C1 is an IP5306-type chip. In FIGS. 11-17, the main control chip A is represented by label U3, the charge and discharge management chip C1 is represented by label U2, the display screen 22 is represented by label J1 and the connecting port C3 of the battery 9 includes a BAT+ portion and a BAT− portion.

Furthermore, the HT66F019 single chip microcomputer U3 includes twenty pins which are respectively designed as a first pin, a second pin, a third pin, a fourth pin, a fifth pin, a sixth pin, a seventh pin, an eighth pin, a ninth pin, a tenth pin, an eleventh pin, a twelfth pin, a thirteenth pin, a fourteenth pin, a fifteenth pin, a sixteenth pin, a seventeenth pin, an eighteenth pin, a nineteenth pin and a twentieth pin. The first pin is grounded, all the second pin, the third pin and the fourth pin are empty, the fifth pin is connected with the seventh resistor R7 and the other end of the seventh resistor R7 is connected with the KEY pin of the charge and discharge management chip U2, and the sixth pin is connected with the keyswitch K1.

The seventh pin is connected with the thirteenth resistor R13, the other end of the thirteenth resistor R13 is connected with the gate of the third P-MOS Q3, and the gate of the third P-MOS Q3 is also connected with the fourteenth resistor R14. The other end of the fourteenth resistor R14 is connected with all the source of the third P-MOS Q3, the twelfth resistor R12 and the source of the first P-MOS Q1. The drains of the first P-MOS Q1 and the third P-MOS Q3 are respectively connected with the display screen J1. The gate of the first P-MOS Q1 is connected with the other end of the twelfth resistor R12 and the seventeenth resistor R17, and the other end of the seventeenth resistor R17 is connected with the thirteenth pin of the HT66F019 single chip microcomputer U3.

All the eighth-twelfth pins of the HT66F019 single chip microcomputer U3 are connected with the display screen J1.

The fourteenth pin is connected with the twentieth resistor R20 of the power amplifying circuit B1, the other end of the twentieth resistor R20 is connected with the base of the fourth NPN-type triode Q4, the emitter of the fourth NPN-type triode Q4 is grounded. The collector of the fourth NPN-type triode Q4 is connected with the twenty-first resistor R21, the other end of the twenty-first resistor R21 is connected with the twenty-second resistor R22 and the gate of the second P-MOS Q2. The other end of the twenty-second resistor R22 is connected with a 5V power supply and the drain of the second P-MOS Q2. The source of the second P-MOS Q2 and the drain of second P-MOS Q2 are respectively connected with the sixteenth resistor R16, at the same time, the source of the second P-MOS Q2 is also connected with a DRIVER port. The DRIVER port is connected with each of the first inductor L1 of the step-up constant current circuit B2, a diode D3, the tenth capacitor C10, a pair of LEDs and the VIN pin o the step-up constant current chip U1.

The fifteenth pin of the HT66F019 single chip microcomputer U3 is connected with the nineteenth resistor R19 and the eighteenth resistor R18, the other end of the nineteenth resistor R19 is grounded and also connected with the BAT− portion, and the other end of the eighteenth resistor R18 is connected with each of the BAT+ portion, one end of the second inductor L2 and the eleventh resistor R11.

The sixteenth resistor R16 of the HT66F019 single chip microcomputer U3 is connected with the SDA port of the charge and discharge management chip U2, and the seventeenth resistor R17 is connected with the SCL port of the charge and discharge management chip U2.

The eighteenth pin of the HT66F019 single chip microcomputer U3 is connected with the eighth resistor R8 and the first resistor R1, the other end of the first resistor R1 is grounded, and the other end of the eighth resistor R8 is connected with the VIN port of the Micro USB connector circuit C2 and the VBUS port of a USB socket.

The nineteenth pin of the HT66F019 single chip microcomputer U3 is connected with the IRQ port of the charge and discharge management chip U2. The VOUT port of the charge and discharge management chip U2 is output a 5V power supply and connected with the ninth capacitor C9, and the other end of the ninth capacitor C9 is grounded. The SW port of the charge and discharge management chip U2 is connected with the other end of the second inductor L2, the BAT port of the charge and discharge management chip U2 is connected with the other end of the eleventh resistor R11 and the seventh capacitor C7, and the other end of the seventh capacitor C7 is grounded.

The twelfth pin of the HT66F019 single chip microcomputer U3 is connected with each of the thirteenth capacitor C13, the seventeenth capacitor C17, the OUT port and the VDD port of the voltage-regulator U4. Both the other end of the thirteenth capacitor C13 and the other end of the seventeenth capacitor C17 are grounded, the IN port of the voltage-regulator U4 is connected with the BAT+ portion, and the GND port of the voltage-regulator U4 is grounded.

In an exemplary embodiment of the present disclosure, the present structure of the present disclosure can some advantageous shown below:

It can achieve a good sterilization effect with 99.9% by the UV light source to sterilize water and have a compact structure.

It can have a high circuit integration structure to greatly reduce the volume of the cup shielding and conveniently carry it.

Water fetched in outdoors can be first filtered by the filter with an activated carbon filtering layer or a PP cotton+ activated carbon filtering layer, and then can be sterilized by covering the cup shielding with a UV sterilization member for sterilization treatment.

The cup body is preferably made of stainless steel, but not limited to stainless steel and is vacuumed therein so that it has the function of heat preservation.

The cup body has a uniform caliber so that cups with different volume can match with a same cup shielding.

The cup shielding is made of environment-friendly food grade material via ultrasonic welding technology so that it is safe and reliable. At the same time, it is made of IP66-class waterproof dust so that its surface can be directly washed with water. There is also a large-capacity lithium battery set in the cup shielding which can be charged by a Micro USB port via only a common charging data line.

A display screen is set on the cup shielding which can at least display its current temperature and power level, and its charging indicator light.

Water fetched in outdoors can reach the standard of healthy drinking water that it is first filtered by the filter and then sterilized by the UV light source.

Although the features and elements of the present disclosure are described as embodiments in particular combinations, each feature or element can be used alone or in other various combinations within the principles of the present disclosure to the full extent indicated by the broad general meaning of the terms in which the appended claims are expressed.

What is claimed is:

1. A UV sterilization cup comprising:
a cup body comprising a first receiving room with a first opening being formed on its portion adjacent to a cup shielding which is covered on the cup body;
the cup shielding comprising a second receiving room with a second opening being formed on its end adjacent to the cup body and connected to the first opening;
a UV sterilization member received in the second receiving room to emit ultraviolet ray and comprising a UV PCB installed in one end of the second receiving room away from the second opening, and a UV light source electrically connected to a UV generating circuit of the UV PCB and installed in the other end of the second receiving room adjacent to the second opening;
a waterproof transparent member received in the cup shielding and adjacent to the first receiving room for sealing the UV sterilization member so as to block connection between the first receiving room and the second receiving room; and wherein
the waterproof transparent member is mounted on a bottom end of the UV light source to abut against the bottom end of the UV light source and configured to transmit the ultraviolet ray emitted from the UV sterilization member into the first receiving room; and wherein
the UV sterilization cup further comprises a filter used in conjunction with the first opening of the cup body; and wherein
the filter comprises a housing with a hollow configuration and opening-setting in its two ends, and a filtering core received in the housing; the housing arranged in two layers at one end adjacent to the end of the first opening and comprising a third cup wall, a fourth cup wall overlapped with the third cup wall successively from the inside to the outside, and a second gap formed between the third cup wall and the fourth cup wall; an opposite end of the first opening adjacent to the cup body inserting into the second gap to connect with the housing, and the filtering core installed on the fourth cup wall.

2. The UV sterilization cup as claimed in claim 1, wherein a wall of the cup shielding is arranged in two layers at a position of the second opening and comprises a first cup wall, a second cup wall overlapped with the first cup wall successively from the inside to the outside, and a first gap formed between the first cup wall and the second cup wall; an end of the first opening inserting into the first gap to connect with the cup shielding, the UV sterilization member installed on a top end of the second cup wall and the waterproof transparent member arranged on the second cup wall and formed below the UV sterilization member.

3. The UV sterilization cup as claimed in claim 2, wherein the first cup wall comprises a first thread formed on its inner wall thereof, and the cup body comprises a second thread formed on an outer wall of the first opening to correspondingly engage with the first thread.

4. The UV sterilization cup as claimed in claim 2, wherein the length of the second cup wall extending along a longitudinal direction of the cup body towards the first opening is greater than that of the first cup wall extending along the longitudinal direction of the cup body towards the first opening, the second cup wall extending into the first receiving room.

5. The UV sterilization cup as claimed in claim 2, wherein the cup shielding further comprises a cover, a main body with a hollow configuration and opening-setting in its two sides, and a frame; the second opening formed on one side of the main body and the first and second cup walls arranged on the one side of the main body, the cover covered on the other side of the main body away from the second opening, the frame tightly fixed in the second cup wall with a battery therein, the cover, the main body and the frame cooperatively surrounding to form the second receiving room; the UV PCB mounted on the other side of the main body adjacent to the cover, the UV light source mounted on the second cup wall and formed on a lower end of the frame to abut against the frame, the waterproof transparent member mounted on the second cup wall and formed on a bottom end of the UV light source to abut against the bottom end of the UV light source.

6. The UV sterilization cup as claimed in claim 5, wherein the frame further comprises an installing plate formed on its upper portion thereon and including a connecting hole thereof, the main body comprising a plurality of supporting steps arranged at intervals for supporting the UV PCB, the installing plate abutting against a top portion of a connecting stud which is formed on the supporting step to connect the connecting stud and the connecting hole via screws.

7. The UV sterilization cup as claimed in claim 5, wherein the UV light source comprises a UV light panel abutting against the lower end of the frame and comprising at least one UV LED formed thereon, and a reflector connected to the UV light panel and comprising a narrow portion abutting against the bottom of the UV light panel and surrounding the at least one UV LED therein, and a wide portion opposite to the narrow portion; the waterproof transparent member comprising a UV transparent plate with high transmittance with its upper portion abutting against the wide portion, a sealing ring surrounding the periphery of the UV transparent plate and interferently fitted with the inner wall of the second cup wall, the main body further comprising a waterproof step protruding out from the inner wall of a lower portion of the second cup wall and abutting against the bottom of the UV transparent plate.

8. The UV sterilization cup as claimed in claim 7, wherein the main body further comprises a waterproof groove formed on the inner wall of the lower portion of the second cup wall for receiving a waterproof sealing sleeve therein.

9. The UV sterilization cup as claimed in claim 5, wherein a plurality of supporting ribs for supporting the UV PCB is arranged at intervals on the circumferential of the main body where the UV PCB is installed.

10. The UV sterilization cup as claimed in claim 5, wherein the main body further comprises a concave portion with a Micro USB port thereof, a silicone ring covered on the concave portion for sealing the Micro USB port, and a Micro USB connector inserted into the Micro USB port to electrically connect with the UV PCB.

11. The UV sterilization cup as claimed in claim 10, wherein the Micro USB port comprises a cap arranged on a position where the silicone ring is installed, the cap rotatably connected to the silicone ring.

12. The UV sterilization cup as claimed in claim 5, wherein the cover further comprises a window formed on its upper end thereof, and a button hole formed adjacent to the window and comprising a key formed thereon for connecting to the UV PCB, a window transparent plate covered on the window and comprising a display screen formed on the bottom thereof to connect to the UV PCB.

13. The UV sterilization cup as claimed in claim 1, wherein the filtering core comprises at least one of an activated carbon filtering core and a PP cotton+ activated carbon filtering core.

14. The UV sterilization cup as claimed in claim 5, wherein the UV generating circuit comprises a main control chip, a step-up driving circuit, a charge and discharge management circuit, a voltage-regulating circuit, a display driving circuit and a keying circuit respectively connected to the main control chip, the main control chip configured to generate a UV generating signal and then drive the UV light source to emit ultraviolet ray according to the UV generating signal amplified by the step-up driving circuit; the charge and discharge management circuit configured to receive a control signal of the main control chip to charge or discharge a battery; the voltage-regulating circuit configured to stabilize the voltage processed by the charge and discharge management circuit and to provide a stabilization power supply for the main control chip; the display driving circuit configured to receive signals of the main control chip and send the signals to a display screen; and the keying circuit configured to receive an input signal from users and then send it to the main control chip.

15. The UV sterilization cup as claimed in claim 14, wherein the charge and discharge management circuit comprises a charge and discharge management chip electrically connected to the main control chip and connected with a connecting port of the battery, and a Micro USB connector circuit connected to the charge and discharge management chip; the charge and discharge management chip configured to receive the control signal of the main control chip and input electronic energy to the connecting port of the battery via the Micro USB connector circuit to charge the battery or output electronic energy to the Micro USB connector circuit via the connecting port of the battery to discharge the battery.

16. The UV sterilization cup as claimed in claim 14, wherein the display driving circuit is configured to drive the display screen to at least display the temperature of fluid that is received in the UV sterilization cup, the power level, the charging indicator and the sterilization timing status.

17. The UV sterilization cup as claimed in claim 14, wherein the step-up driving circuit comprises a power amplifying circuit and a step-up constant current circuit with a step-up constant current chip therein, and the voltage-regulating circuit comprising a voltage regulator therein.

\* \* \* \* \*